United States Patent [19]

Kvita et al.

[11] Patent Number: 4,476,305

[45] Date of Patent: Oct. 9, 1984

[54] 2-SUBSTITUTED 5-VINYLPYRIMIDINES, POLYMERS OBTAINABLE THEREFROM AND PREPARATION THEREOF

[75] Inventors: Vratislav Kvita, Reinach, Switzerland; Jürgen Kaschig, Ardsley, N.Y.

[73] Assignee: Ciba-Geigy Corporation, Ardsley, N.Y.

[21] Appl. No.: 385,586

[22] Filed: Jun. 7, 1982

[30] Foreign Application Priority Data

Jun. 10, 1981 [CH] Switzerland .......................... 3793/81

[51] Int. Cl.³ .................. C07D 401/04; C07D 403/04
[52] U.S. Cl. .................................... 544/296; 526/262; 544/333
[58] Field of Search ............................... 544/296, 333

[56] References Cited

FOREIGN PATENT DOCUMENTS 0045277 7/1981 European Pat. Off. .

OTHER PUBLICATIONS

Kvita, et al., "Chemical Abstracts", vol. 98, 1983, Col. 98:161297r.
Furue et al., Polymer Preprints, Japan, vol. 29, No. 2, p. 280, (1980).
Card et al., Inorganic Chemistry, vol. 17, No. 9, pp. 2345–2349, (1978).

Primary Examiner—Glennon H. Hollrah
Assistant Examiner—James H. Turnipseed
Attorney, Agent, or Firm—Michael W. Glynn

[57] ABSTRACT

The invention relates to 2-substituted 5-vinylpyrimidines of the formula

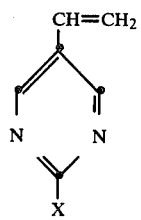

(I)

wherein X is 2-pyridyl or 2-pyrimidyl, unsubstituted or substituted by methyl or ethyl groups. The compounds of formula (I) are suitable for the preparation of complex-forming or complexed, uncrosslinked or crosslinked polymers. Complexed polymers obtainable therefrom may be used as catalysts. Polymers complexed with Pd are particularly suitable for transvinylation reactions. Non-complexed polymers obtainable from compounds of formula (I) are suitable for use as metal ion extractors for different applications.

5 Claims, No Drawings

2-SUBSTITUTED 5-VINYLPYRIMIDINES, POLYMERS OBTAINABLE THEREFROM AND PREPARATION THEREOF

The present invention relates to novel 2-substituted 5-vinylpyrimidines, polymers obtainable therefrom, to a process for the preparation thereof and to the novel intermediates developed for obtaining the 2-substituted 5-vinylpyrimidines.

Up to now it has been possible to obtain vinylpyrimidines only by complicated multistep syntheses [q.v. for example J. Am. Chem. Soc. 76 1878 (1954), J. Het. Chem. 11, 295 (1974) and Polymer 19, 542 (1978)]. 5-Vinylpyrimidines are suitable for obtaining complex-forming polymers; however, the complex-forming action of such polymers is relatively insignificant. Complex-forming polymers containing bipyridine radicals as well as transition metal complexes thereof are also known from the literature [q.v. for example U.S. Pat. No. 3,810,888; German Offenlegungsschrift specifications Nos. 2 037 412 and 2 049 057; Polymer Preprints, Japan, 29, 2, 280 (1980); Inorgan. Chem. 17, No. 9, 2345 (1978); J. Org. Chem. 44, 1095 (1978) and 43, 2958 (1978); J. Am. Chem. Soc. 100:21, 6635 (1978); and Inorg. Chim. Acta 33, L 139 (1979) and 44, L 289 (1980)].

It has now been found that novel 5-vinylpyrimidines of the formula I

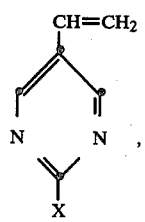  (I)

wherein X is

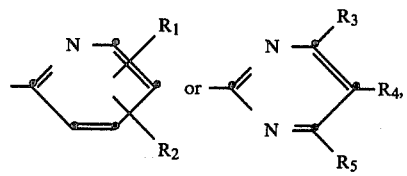

and each of $R_1$ to $R_5$ independently of the other is hydrogen, methyl or ethyl, may be prepared in very simple and economic manner by reacting 5-formyl-α-pyrone, in the presence of an organic solvent, with an amine of the formula II $HN(R_6)(R_7)$  (II)

to give a compound of the formula III

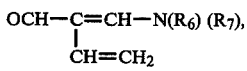  (III)

and reacting said compound of the formula III with a compound of the formula IV

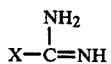  (IV)

in which formulae above X is as defined for formula I, each of $R_6$ and $R_7$ independently of the other is straight chain or branched alkyl which contains up to 10 carbon atoms and is unsubstituted or substituted by an OH group, or $R_6$ and $R_7$ together are $-C_pH_{2p}-$ or $-(CH_2)_2$, and p is an integer from 2 to 22.

Where X is a

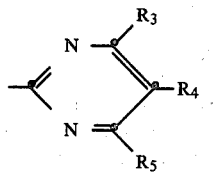

group, each of $R_3$, $R_4$ and $R_5$ is preferably hydrogen, methyl or ethyl. In further preferred compounds, each of $R_3$ and $R_5$ is methyl and $R_4$ is hydrogen, or $R_3$ is methyl or ethyl and each of $R_4$ and $R_5$ is hydrogen. The most preferred compounds of the formula I are those in which X has the given meaning, $R_1$, $R_2$ and $R_4$ are hydrogen and $R_3$ and $R_5$ are methyl, or each of $R_1$ to $R_5$ is hydrogen.

Alkyl groups $R_6$ and/or $R_7$ are e.g. methyl, ethyl, n-propyl, isopropyl, n-butyl, isobutyl, sec-butyl, n-pentyl, 2-methylbutyl, 2,2-dimethylpropyl, n-hexyl, n-heptyl, 1-methylhexyl, 1-ethylhexyl, n-octyl, n-decyl, 2-hydroxyethyl, 2- or 3-hydroxypropyl, 4-hydroxybutyl, 6-hydroxyhexyl or 8-hydroxyoctyl. Preferred alkyl groups are straight chain alkyl groups containing 1 to 8 carbon atoms and $-(CH_2)_n-CH(CH_3)_2$ groups, wherein n is 0 or an integer from 1 to 3, preferably isopropyl, isobutyl and isopentyl (2-methylbutyl). $R_6$ and $R_7$ together as a $-C_pH_{2p}-$group may be a straight chain or branched radical. Preferred straight chain radicals $-C_pH_{2p}-$ are those containing 2 to 7, in particular 2 to 5, carbon atoms. Branched radicals $-C_pH_{2p}-$ formed by $R_6$ and $R_7$ are preferably radicals of the formula V $$-\underset{R_{11}}{CH}-\underset{R_8}{CH}-\underset{R_9}{CH}-\underset{R_{10}}{CH}-\underset{R_{12}}{CH}- \quad (V)$$

wherein each of $R_8$ to $R_{10}$ independently of the other is hydrogen or straight chain or branched $C_1$–$C_5$ alkyl and each of $R_{11}$ and $R_{12}$ independently of the other is hydrogen or methyl, with the proviso that at least one of $R_8$ to $R_{12}$ differs from hydrogen. Examples of straight chain or branched alkyl groups $R_8$ to $R_{10}$ are methyl, ethyl, n-propyl, iso-propyl, n-butyl, sec-butyl, n-pentyl and isopentyl. The preferred alkyl group is ethyl, with methyl being most preferred. Preferred radicals of the formula V are those wherein each of $R_{11}$ and $R_{12}$ is methyl and each of $R_8$ to $R_{10}$ is hydrogen.

As compounds of the formula II it is preferred to use those in which each of $R_6$ and $R_7$ independently of the other is straight chain $C_1$–$C_8$ alkyl, preferably $C_1$–$C_4$ alkyl, or $R_6$ and $R_7$ together are $-(CH_2)_x$, in which x is 2 to 5, or $-(CH_2)_2-O-(CH_2)_2$. It is especially preferred to use compounds of the formula II, wherein each of $R_6$ and $R_7$ independently of the other is methyl or ethyl or together are a —(CH$_2$)$_2$—O—(CH$_2$)$_2$— or —(CH$_2$)$_5$— group. Most preferably, each of R$_6$ and R$_7$ is methyl or ethyl or together form the —(CH$_2$)$_5$— group.

The concentration of the 5-formyl-α-pyrone and the amine of the formula II in the organic solvent is conveniently in the range from 5 to 50% by weight, preferably from 10 to 40% by weight and, most preferably, from 25 to 30% by weight. It is advantageous to use equimolar amounts of the 5-formyl-α-pyrone and the amine of the formula II.

Suitable organic solvents for the reaction of the 5-formyl-α-pyrone with the amine of the formula II are e.g. cycloaliphatic or aromatic hydrocarbons such as cyclohexane, benzene, toluene and xylenes; aliphatic or cyclic ethers such as diethyl ether, dioxan and tetrahydrofuran; chlorinated aliphatic hydrocarbons such as methylene chloride, chloroform, tetrachloromethane, trichloroethylene and dichloroethane; C$_{1-4}$ alkyl esters of lower aliphatic monocarboxylic acids such as methyl acetate, ethyl acetate and n-butyl acetate; ethylene glycol dimethyl or diethyl ether; alkanols containing up to 6 carbon atoms such as methanol, ethanol, n-propanol, isopropanol and butanol; aliphatic ketones such as acetone; cyclic amides such as N-methylpyrrolidone; N,N-dialkylamides of lower aliphatic monocarboxylic acids such as N,N-dimethylformamide and N,N-dimethylacetamide; dialkylsulfoxides such as dimethylsulfoxide and diethylsulfoxide; hexamethylphosphoric triamide and sulfolane; alkylnitriles containing 2 to 5 carbon atoms such as acetonitrile, propionitrile and butyronitrile; and cyclic amines such as pyridine, picoline and lutidine.

Preferred solvents are benzene, dioxan, ethylene glycol dimethyl and diethyl ether, methanol, ethanol, dimethyl sulfoxide and acetonitrile. Particularly preferred solvents are benzene, dioxan and dimethylsulfoxide, with acetonitrile being most preferred. The reaction temperatures for the reaction of the 5-formyl-α-pyrone with the amine of formula II may vary within wide limits and are conveniently in the range from 20° to 100° C. The most preferred temperature range is from 25° to 40° C. The formyl-α-pyrone and the compounds of formula II are known or may be prepared in a manner which is known per se.

The intermediates of the formula III, which have been specially developed for the preparation of the compounds of formula I, are novel and likewise constitute an object of the present invention. In this connection, what has been said above applies with respect to preferred meanings of R$_6$ and R$_7$ in compounds of the formula III. The compounds of formula III may be isolated, if desired, e.g. by high vacuum distillation or chromatography over silica gel. Depending on the nature of the substituents R$_6$ and R$_7$, suitable eluants are e.g. chloroform or mixtures of chloroform and acetone. bjIn general, however, it is not necessary to isolate the compounds of formula III. The reaction solutions containing the compounds of formula III are conveniently reacted direct with the amidines of the formula IV (consecutive reaction without isolation of the intermediates). As the amidines of the formula IV are normally not very stable, they are preferably set free with suitable bases from their salts, e.g. the hydrochlorides, before the reaction in a manner which is known per se. Preferred bases are alkali metal alcoholates or alkaline earth alcoholates such as magnesium ethylate, sodium or potassium methylate, and sodium or potassium tert-butylate. The most preferred base is sodium methylate.

Alcoholates isolated beforehand, in suitable solvents, preferably in those employed for obtaining the compounds of formula III, may be used; or else the alcoholate is formed in situ from the alkaline earth metal or alkali metal and excess alcohol. Finally, the amidines may be set free e.g. also in a polar aprotic solvent such as dioxan, tetrahydrofuran, ethyl acetate, ethylene glycol dimethyl or diethyl ether, N,N-dimethylformamide, N,N-dimethylacetamide, N-methylpyrrolidone, dimethylsulfoxide, hexamethylphosphoric triamide or sulfolane, by adding an equimolar amount of sodium hydride to a suspension of the amidine salt in one of these solvents. In a preferred embodiment, the solutions so obtained of the amidines (amidine bases) are then mixed with the reaction solutions containing the compounds of formula III and reacted in the temperature range of 25° to 90° C., preferably from 60° to 80° C. The compounds of formula I can then be isolated in conventional manner and, if desired, purified, e.g. by chromatography or sublimation or by a combination of these methods.

The compounds of formula I are valuable starting materials for the preparation of complex-forming or complexed polymers.

Accordingly, the invention relates also to novel cross-linked or uncrosslinked polymers which are obtainable by polymerising 2 to 100 mole % of a compound of the formula I and 0 to 98 mole % of a compound of the formula (A)

in which X$_1$ is hydrogen, X$_2$ is hydrogen, chlorine or methyl and X$_3$ is hydrogen, methyl, chlorine, —CN, —COOH, —CONH$_2$, phenyl, methylphenyl, methoxyphenyl, cyclohexyl, pyridyl, imidazolyl, pyrrolidyl, —COO—alkyl containing 1 to 12 carbon atoms in the alkyl moiety, —COO—phenyl,

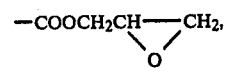

—COO—alkyl—OH containing 1 to 4 carbon atoms in the alkyl moiety, —OCO—alkyl containing 1 to 4 carbon atoms in the alkyl moiety, —OCO—phenyl, —CO—alkyl containing 1 to 3 carbon atoms in the alkyl moiety, alkoxy containing 1 to 20 carbon atoms or phenoxy, or X$_2$ is hydrogen and X$_1$ and X$_3$ together are an anhydride grouping, a —CO—NR'''—CO—grouping or each is —COOh or —COO—alkyl containing 1 to 6 carbon atoms in the alkyl moiety and R''' is straight chain or branched C$_{1-18}$alkyl, cyclohexyl or phenyl which C$_{1-1-}$ $_6$alkyl, halogen, cyano, nitro and/or C$_{1-3}$alkoxy, in the presence of 0 to 60 mole % of a polyunsaturated crosslinking agent and, if desired, converting complex-forming polymers so obtained into polymers which are wholly or partially complexed with metals other than alkali metals or alkaline earth metals, or with metal compounds other than alkali metal compounds or alkaline earth metal compounds.

Furthermore, the crosslinking may also be effected by coordination of the metal atom, such as copper, iron or ruthenium, with further structural units derived from compounds of the formula I.

Preferred compounds of the formula (A) are those in which $X_1$ is hydrogen, $X_2$ is hydrogen or methyl and $X_3$ is phenyl, pyridyl, —COO—alkyl—OH containing 2 to 4 carbon atoms in the alkyl moiety or —COO—alkyl containing 1 to 12 carbon atoms in the alkyl moiety. Styrene is most preferred.

Examples of suitable polyunsaturated crosslinking agents are divinylbenzenes, divinylpyridines, divinyltoluenes, divinylnaphthalenes, divinylxylenes, divinylethylbenzenes, divinylsulfone, divinyl ketone, divinyl sulfide, divinyl sebacate, trivinylbenzenes, trivinylnaphthalenes and polyvinylanthracene; ethylene glycol diacrylate, ethylene glycol dimethacrylate, allyl acrylate, diallyl phthalate, diallyl maleate, diallyl fumarate, diallyl succinate, diallyl carbonate, diallyl malonate, diallyl oxalate, diallyl adipate, diallyl sebacate, diallyl tartrate, diallyl silicate, triallyl tricarballylate, triallyl aconitate, triallyl citrate, triallyl phosphate, N,N'-methylenediacrylamide, N,N'-methylenedimethylacrylamide, N,N'-ethylenediacrylamide, and polyallyl ethers and polyvinyl ethers of ethylene glycol, propanetriol, pentaerythritol, resorcinol and the monothio or dithio derivatives of ethylene glycol. The crosslinking agent is preferably employed in an amount of 1 to 30 mole %. Preferred crosslinking agents are divinylpyridine and, in particular, divinylbenzene. The degree of swelling of the polymers can be adapted to the desired specific applications by suitable choice of the comonomers and/or crosslinking agents.

Preferred linear polymers are those which have an average molecular weight from 1,000 to 5,000,000 and which consist of 3 to 100 mole % of recurring structural units of the formula (B)

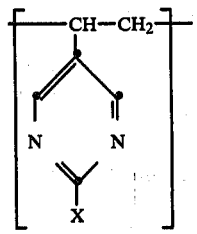

(B)

and/or complexes of such structural units with metals other than alkali metals or alkaline earth metals, or with metal compounds other than alkali metal compounds or alkaline earth metal compounds, and of 0 to 97 mole % of recurring structural units of the formula (C)

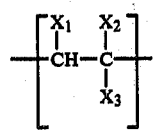

(C)

in which X and $R_1$ to $R_5$ are as defined for formula I and $X_1$, $X_2$ and $X_3$ are as defined for formula (A), in particular those polymers of this type which have an average molecular weight from 2,000 to 3,000,000, and which consist of 3 to 100 mole % of recurring structural units of the formula (B), and/or of complexes of such structural units of the formula (B), and of 0 to 97 mole % of recurring structural units of the formula (C), with $R_1$ to $R_5$, $X_1$, $X_2$ and $X_3$ having the preferred meanings assigned to them previously and 5 to 100 percent of the structural units of the formula (B) being complexed with metals other than alkali metals or alkaline earth metals, or with metal compounds other than alkali metal compounds or alkaline earth metal compounds. Most preferred are those linear polymers having an average molecular weight of 2000 to 1,500,000 and/or complexes thereof which consist only of structural units of the formula (B) and/or complexes thereof, wherein X is as defined for formula I, $R_1$, $R_2$ and $R_4$ are hydrogen and $R_3$ and $R_5$ are methyl, or each of $R_1$ to $R_5$ is hydrogen, and 5 to 100 percent of the structural units of the formula (B) are complexed as described herein.

The above linear polymers may be obtained by polymerising 3 to 100 mole % of a compound of the formula I with 0 to 97 mole % of a compound of the formula (A) and, if desired, subsequently converting complex-forming polymers so obtained into polymers which are wholly or partially complexed with metals other than alkali metals or alkaline earth metals, or with metal compounds other than alkali metal compounds or alkaline earth metal compounds.

The polymerisation of compounds of the formula I and their copolymerisation with compounds of the formula (A), if appropriate in the presence of polyunsaturated crosslinking agents, may be carried out in a manner known per se, for example in the presence of conventional anionic initiators. Free-radical polymerisation is preferred. In this reaction, it is advantageous to use about 0.01 to 5% by weight, preferably 0.01 to 1.5% by weight, based on the total weight of the monomers and optional crosslinking agents, of free-radical initiators known per se, such as inorganic or organic peroxides or azo compounds, for example hydrogen peroxide, potassium peroxydisulfate, tert-butyl hydroperoxide, di-tert-butyl peroxide, peracetic acid, dibenzoyl peroxide, diacyl peroxides, cumene hydroperoxide, tert-butyl perbenzoate, tert-alkyl peroxydicarbonates and $\alpha,\alpha'$-azoisobutyronitrile. The reaction temperatures for the free-radical polymerisation are in general in the range from about 30° to 100° C. The free-radical polymerisation may however, also be carried out at low temperature, for which purpose redox systems may also be used in the abovementioned concentrations, e.g. mixtures of peroxides, such as hydrogen peroxide, and a reducing agent, such as divalent iron ions. The polymerisation may be carried out in homogeneous phase, for example in substance or in solution, or in a heterogeneous phase, i.e. as precipitation polymerisation, emulsion polymerisation or suspension polymerisation. Polymerisation in solution is preferred. Examples of suitable solvents are toluene, N,N-dimethylformamide, N,N-dimethylacetamide and acetonitrile.

The metals used for forming complexes with compounds of the formula I are, for example, those of main groups IIIa and IVa and of sub-groups IVb, Vb, VIb, VIIb, VIII, Ib and IIb of the Periodic Table. Metal compounds which are suitable for the preparation of complexes of the invention, or in such complexes, are preferably neutral or ionic metal compounds of the abovementioned main groups and sub-groups of the Periodic Table, for example salts or acids, while in salts the metal may be present either in the anion or in the cation. If desired, the metal atom of the complex, or that of the metal compounds used for the preparation thereof, may additionally also have further coordinative, covalent or ionic bonds which link it to other ions, atoms, molecules or parts of molecules such as structural units of a polymer, for example to one or more further compounds of the formula I or structural units of a polymer derived therefrom, or to a 2,2'-bipyridine radical.

The salts may be salts with either inorganic or organic acids such as halides, in particular chlorides, nitrates, sulfates, phosphates, perchlorates and carboxylates; such as formates, acetates, propionates and stearates; and also salts which contain a complex anion or cation, for example oxo derivatives of titanium, vanadium, zirconium, molybdenum, hafnium, niobium, tantalum, tungsten and uranium; and anionic metal complexes of halide, cyanide, thiocyanate, thiosulfate and orthophosphate ions, such as tetrachloroplatinate, tetrachloropalladate or hexathiocyanatochromate. Examples of such salts or complexes are: stannyl chloride, lead acetate; copper(I) or copper (II) chloride, bromide or iodide, copper(II)acetate, nitrate or sulfate, copper-(I)cyanide, tetraacetonitrilo-copper(I) perchlorate; silver nitrate; zinc chloride, cyanide and thiocyanate, cadmium chloride, cyanide and thiocyanate, mercury iodide or cyanide; zirconium tetrachloride; vanadium-(III)chloride, vanadium oxysulfate, ammonium metavanadate, niobium(V)chloride, tantalum(V)chloride, uranium tetrachloride or tetrabromide, uranyl nitrate and acetate; chromium carbonyl, chromium(III)chloride, hexathiocyanatochromate, molybdenum oxytrichloride, molybdenum carbonyl, tungsten oxytrichloride, tungsten carbonyl; manganese(II)chloride and iodide; iron(III)nitrate, phosphate, sulfate or acetate, iron(II) or iron(III)chloride, ruthenium (III)chloride, potassium pentachlorohydroxyruthenate(IV), dichloro-bis-(2,2'-bipyridine)-ruthenium(II), cobalt(II) chloride, cobalt(II)acetate, nitrate or sulfate, rhodium(II) acetate, rhodium(III)chloride, potassium rhodium chloride, nickel(II)acetate, nickel(II)bromide or chloride, nickel-(II) sulfate, palladium(II)chloride or iodide, palladium-(IV) chloride, palladium acetate, palladium nitrate, potassium tetrachloropalladate, potassium tetrachloroplatinate and potassium hexachloroplatinate.

Preferred complexes are complexes with metals and metal compounds of sub-groups Ib, IIb, IVb, Vb, VIb, VIIb and VIII, and especially metals and metal compounds of sub-groups Ib and VIII. Most preferred are polymers in which the complexed central atom is iron, ruthenium, palladium, rhodium, cobalt, nickel, platinum or copper, more particularly ruthenium, palladium, cobalt, platinum or copper and most particularly palladium or cobalt.

Suitable acids are e.g. acids which correspond to the abovementioned salts with a complex anion, such as $H_2PtCl_6$ or $H_2PdCl_4$.

If metal complexes are used for complexing the polymers, those metal complexes are preferred which have at least two readily replaceable ligands which are capable of ligand exchange. The valency of the metal complexed is determined by the nature of the metal compounds employed for the complexing, or by an oxidation or reduction reaction during or after the complexing.

The conversion of the polymers into complexes is carried out in a manner known per se, e.g., by contacting the polymers with a solution or suspension of a suitable metal compound. Examples of suitable reaction media are water, N,N-dimethylformamide, N,N-dimethylacetamide, acetonitrile, dioxan and tetrahydrofuran. The metal compounds used may be e.g. metal salts or acids of the type mentioned above, especially halides or carboxylates, or metal complexes having at least two replaceable coordinated ligands which can undergo a a ligand exchange, such as tetraacetonitrilo-copper(I)perchlorate, dichloro-bis-(2,2'-bipyridine)-ruthenium(II-)and potassium tetrachloroplatinate.

The wholly or partially complexed polymers which are prepared according to the invention may be employed as catalysts, for example as hydrogenation catalysts for the hydrogenation of alkenes or alkynes, as isomerisation catalysts or as catalysts for the acetoxylation of benzene.

Polymers which are at least partially complexed with palladium or a palladium compound, in particular palladium acetate, may be used in particular as very efficient catalysts for transvinylation reactions. Their activity is comparable with that of the homogeneous catalysts which are generally used for transvinylation reactions. Compared with previously known transvinylation catalysts such as potassium tetrachloropalladate, they have the advantage of being directly re-usable for further reactions, without reprocessing.

Uncomplexed polymers of this invention can be used for the preparation of corresponding complexed polymers. Such complex-forming polymers are, however, also used as metal ion extractors, for example for the extraction of noble metals, rare earths, and radioactive elements such as uranium, from their ores or minerals, for the separation of radioactive cesium from other metals, or for the separation of different metals (with the exception of alkali metals and alkaline earth metals), for the recovery of chromium salts from tannery effluents, for the demineralisation of organic solvents without introducing extraneous ions, for the preparation of dielectric fluids, and for the purification of industrial effluents in order to remove undesired metal ions.

After the binding of the metal ions, the complexes may be reconverted into the complex-forming polymers or complex-forming compounds of the formula I, for example by elution with strong acids or with complex-forming agents such as ethylenediamine or ethylenediaminetetraacetic acid.

Using the compounds of the formula I and their complexes it is possible to prepare linear polymers having virtually any desired average molecular weight. By using suitable comonomers and/or crosslinking agents, so-called tailor-made polymers can be prepared, i.e. polymers of which the composition and the number of complex-forming or complexed pyrimidine units is adapted to the specific end uses. The crosslinked or uncrosslinked polymers which can be prepared using the compounds of the formula I and complexes thereof have in addition a high stability to thermal or chemical degradation. The following Examples illustrate the invention in more detail.

(A) PREPARATORY EXAMPLES

EXAMPLES 1-12

Preparation of compounds of the formula III

Equimolar amounts of 5-formyl-α-pyrone and amine of the formula II are dissolved in the solvents indicated in the following table. Each solution is stirred until the evolution of carbon dioxide from the solution ceases. The further reaction conditions and the NMR spectral data of the compounds of formula III are given in the table. The so obtained compounds of formula III may be used direct for further reaction.

TABLE

Compounds of formula III

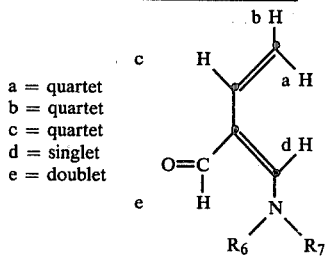

a = quartet
b = quartet
c = quartet
d = singlet
e = doublet

| Example | R₆ = R₇ | Solvent | Time (hr.) | T (°C.) | a ppm | b ppm | c ppm | d ppm | e ppm | $J_{ab}$ (Hz) | $J_{ce}$ (Hz) | $J_{ac}$ (Hz) | $J_{bc}$ (Hz) |
|---|---|---|---|---|---|---|---|---|---|---|---|---|---|
| 1 | methyl | CD₃CN(*) | 5 | 40 | 5.60 | 5.10 | 6.58 | 6.70 | 8.97 | 3 | 1 | 17 | 11 |
| 2 | ethyl | benzene (d₆) | 2 | 25 | 6.10 | 5.25 | 6.50 | 6.30 | 9.28 | | (compounds | | |
| 3 | n-pentyl | CD₃CN | 5 | 25 | 5.60 | 5.10 | 6.40 | 6.65 | 8.95 | | 1–12) | | |
| 4 | n-octyl | CD₃CN | 8 | 25 | 5.60 | 5.08 | 6.38 | 6.62 | 8.94 | | | | |
| 5 | isopropyl | CD₃CN | 7 | 25 | 5.59 | 5.10 | 6.37 | 6.80 | 9.01 | | | | |
| 6 | isobutyl | CD₃CN | 5 | 25 | 5.50 | 5.20 | 6.48 | 6.72 | 9.00 | | | | |
| 7 | 2-methylbutyl | CD₃CN | 5 | 25 | 5.60 | 5.10 | 6.40 | 6.64 | 8.84 | | | | |
| 8 | —CH(CH₃)—(CH₂)₃—CH(CH₃) | CD₃CN | 10 | 25 | 5.60 | 5.08 | 6.41 | 6.62 | 8.94 | | | | |
| 9 | —(CH₂)₃— | CD₃CN | 3 | 40 | 5.84 | 5.00 | 6.40 | 6.55 | 8.92 | | | | |
| 10 | —(CH₂)₄— | dimethylsulfoxide (d₆) | 5 | 40 | 5.75 | 4.93 | 6.53 | 6.99 | 8.90 | | | | |
| 11 | —(CH₂)₅— | CD₃CN | 2 | 25 | 5.50 | 5.10 | 6.38 | 6.68 | 8.93 | | | | |
| 12 | —(CH₂)₂—O—(CH₂)₂ | CD₃CN | 2 | 25 | 5.47 | 5.14 | 6.38 | 6.70 | 8.96 | | | | |

(*)CD₃CN = trideuteroacetonitrile

Example 13

2-Pyrimidyl-5-vinylpyrimidine 53.32 g (0.43 mole) of 5-formyl-α-pyrone are dissolved in 344 ml of acetonitrile and to this solution are added 36.98 g (0.43 mole) of piperidine, while cooling with ice. Vigorous evolution of carbon dioxide commences almost immediately. The reaction is complete after stirring for 2 hours at room temperature (24° C.).

In a separate reaction vessel, 75.44 g (0.43 mole) of sodium methylate in 260 ml of methanol are added to 67.56 g (0.43 mole) of pyrimidylamidine hydrochloride in order to set free the 2-pyrimidine-amidine base. The acetonitrile solution of α-vinyl-β-piperidylacrolein is mixed with the methanolic solution of the 2-pyrimidine-amidine base and the mixture is refluxed for 6 hours. [The full reaction course may be followed by thin-layer chromatography, although the α-vinyl-β-piperidylacrolein has the same $R_f$ value as the 2-pyrimidyl-5-vinyl-pyrimidine (silica gel, thin-layer plate; eluant=chloroform/acetone in the volume ratio 9:1). The stain of the educt turns brown after spraying with ninhydrin and heating the plate, whereas the stain of the product remains colourless after the same treatment]. The reaction mixture is then filtered and the filtrate is evaporated to dryness. The crude product is chromatographed over a column of silica gel (1000 g of SiO₂) with chloroform/acetone in the volume ratio 9:1 as eluant. The product is sublimed at 130° C./10⁻² bar, affording 15.8 g (20% of theory) of 2-pyrimidyl-5-vinylpyrimidine with a melting point of 150° C.

Analysis for C₁₀H₈N₄(mol. wt. 184.2): calculated: C 65.21%; H 4.38%; N 30.42%. found: C 65.10%; H 4.59%; N 30.12%.

NMR spectrum: vinyl group δ=5.58 ppm (1H, doublet (J=10Hz), 6.00 ppm (1H, doublet, J=18 Hz), 6.75 ppm (1H, quartet, J=18 Hz and J=10Hz). Pyrimidine rings δ=7.40 ppm (1H, triplet, J=5 HZ), 9.05 ppm, (2H, doublet, J=5 Hz), 9.05 ppm (2H, singlet).

EXAMPLE 14

2-Pyridyl-5-vinylpyrimidine 10.54 g (0.058 mole) of 5-formyl-α-pyrone are dissolved in 68 ml of acetonitrile and to this solution are then added 7.31 g (0.085 mole) of piperidine, while cooling with ice. Vigorous evolution of carbon dioxide commences. The reaction is complete after stirring for 2 hours at room temperature (24° C.). In a separate reaction vessel, 13.34 g(0.085 mole) of 2-pyridylamidine hydrochloride are added to a solution of sodium methylate [consisting of 1.96 g(0.059 gram atom) of sodium and 68 ml of methanol] in order to set free the 2-pyridylamidine base. The acetonitrile solution of α-vinyl-β-piperidylacrolein is mixed with the methanolic solution of the β-pyridylamidine base and the reaction mixture is refluxed for 12 hours. The reaction mixture is then filtered with suction and the pH is adjusted to 4 with acetic acid. The aqueous solution is extracted with three 200 ml portions of chloroform. The extracts are evaporated to dryness and the distillation residue is chromatographed over a column of 250 g of silica gel with chloroform/methanol in the volume ratio 9:1 as eluant. The residue obtained after concentrating the eluant mixture is extracted hot with six 50 ml portions of cyclohexane and 2-pyridyl-5-vinylpyrimidine crystallises from the combined extracts. This product is sublimed at 90° C./10⁻² bar, affording 5.44 g (35% of theory) of 2-pyridyl-5-vinylpyrimidine with a melting point of 103° C.

Analysis for C₁₁H₉N₃ (mol. wt. 183.21): calculated: C 72.12%; H 4.95%; S 22.94%. found: C 71.86%; H 4.99%; S 23.00%.

NMR spectrum: vinyl group δ=5.48 ppm (1H, doublet, J=11Hz), 5.91 ppm (1H, doublet, J=18 Hz), 6.70 ppm (1H, quartet, J=18 Hz and J=11 Hz); pyridine ring δ=7.36 ppm (1H, octet, J=5 Hz, J=8 Hz, J=1Hz), 7.82 ppm (1H, sextet, J=8 Hz, J=8 Hz, J=2 Hz), 8.40 ppm (1H, quartet, J=8 Hz, J=1 Hz), 8.86 ppm (1H, quartet, J=5 Hz, J=2 Hz).

EXAMPLE 15

In a manner similar to that described in Example 13, a solution of α-vinyl-β-piperidylacrolein is prepared from 12.94 g (0.104 mole) of 5-formyl-α-pyrone and 8.84 g or 10.26 ml (0.104 mole) of piperidine in 84 ml of acetonitrile. In a separate reaction vessel, 18.31 g (0.104 mole) of sodium methylate in 70 ml of methanol are added to 19.46 g (0.104 mole) of 4,6-dimethylpyrimidylamidine hydrochloride in order to set free the corresponding base. The acetonitrile solution of α-vinyl-β-piperidylacrolein is then mixed with the methanolic suspension of the 4,6-dimethyl-2-pyrimidine-amidine base and the reaction mixture is refluxed for 3 hours, while adding dropwise 6.24 g, i.e. 5.88 ml (0.104 mole), of glacial acetic acid. The suspension is filtered with suction and the filtrate is washed with 20 ml of methanol. The filtrate is evaporated to dryness and the residue is chromatographed over a column of silica gel (1000 g of SiO$_2$) with chloroform/methanol in the volume ratio 19:1 as eluant. The product (14.1 g=63.95% of theory) is stirred in diethyl ether, filtered with suction and dried at 80° C./100 bar, affording 13.42 g (60.86% of theory) of 4,6-dimethyl-2-pyrimidyl-5-vinyl-pyrimidine with a melting point of 230°–232° C. The product is readily sublimable at 160° C./2×10$^{-3}$ bar. The melting point is not raised thereby.

Analysis for C$_{12}$H$_{12}$N$_4$ (mol. wt. 212.26): calculated: C 67.90%; H 5.70%; N 26.40%. found: C 67.93%; H 5.76%; N 26.55%.

NMR spectrum: vinyl group δ=5.57 ppm (1H, doublet, J=10 Hz), 6.01 ppm (1H, doublet, J=18 Hz), 6.79 ppm (1H, quartet, J=18 Hz and J=10 Hz). Pyrimidine rings δ=7.16 ppm (1H, singlet), 9.02 ppm (2H, singlet), 2.69 ppm (6H, singlet).

EXAMPLE 16

{Poly 1-[2-(pyridin-2-yl)-pyrimidin-5-yl]ethylene}

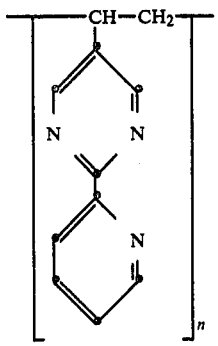

In an ampoule flushed with nitrogen, a solution of 1.5 g of 2-pyridyl-5-vinylpyrimidine in 3 ml of N,N-dimethylacetamide is mixed with 4.03 mg (0.3 mole %) of azoisobutyronitrile and the mixture is heated for 16 hours to 70° C. with the exclusion of air. The resultant highly viscous mixture is dissolved in chloroform and the solution is poured into about 300 ml of diethyl ether to give a white powder. Yield: 1.35 g (90% of theory). Intrinsic viscosity (in chloroform): [η]=0.49 dl/g; average molecular weight $\overline{M}_w$=141,000.

(b) In similar manner, 1.5 g of 2-pyridyl-5-vinyl-pyrimidine are polymerised in 3 ml of toluene. A precipitation polymer is obtained. Yield: 1.42 (95%). Intrinsic viscosity (in chloroform): [η]=0.453 dl/g; average molecular weight $\overline{M}_w$=162,000.

EXAMPLE 17

Poly{1-[2-(pyrimidin-2-yl)-pyrimidin-5-yl]ethylene}

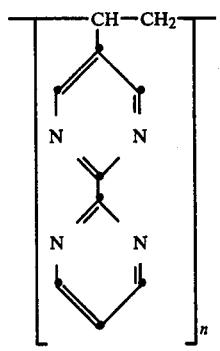

A solution of 2.2 g of 2-pyrimidyl-5-vinylpyrimidine in 7.5 g of N,N-dimethylacetamide is mixed with 5.86 mg (0.3 mole %) of azoisobutyronitrile and polymerisation is effected as in Example 16. The heterogeneous reaction mixture is dissolved in methanol and the product is precipitated from 2.5 ml of toluene. Yield: 1.86 g (85% of theory). Intrinsic viscosity (in methanol) [η]=0.29 dl/g. Average molecular weight $\overline{M}_w$=330,000.

EXAMPLE 18

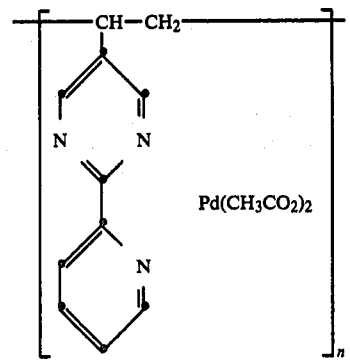

A solution of 400 mg (1.78 mmoles) of palladium(II) acetate in 15 ml of tetrahydrofuran is added dropwise under nitrogen to a solution of 275 mg (1.5 mmoles) of the polymer obtained in Example 16. The reaction mixture is then stirred for 16 hours at 23° C. The yellowish brown precipitate is filtered with suction and washed with about 500 ml of tetrahydrofuran. Yield: 0.53 g (87% of theory). The product has a palladium content of 24.9% by weight. Molar ratio of N:Pd=3:0.93.

EXAMPLE 19

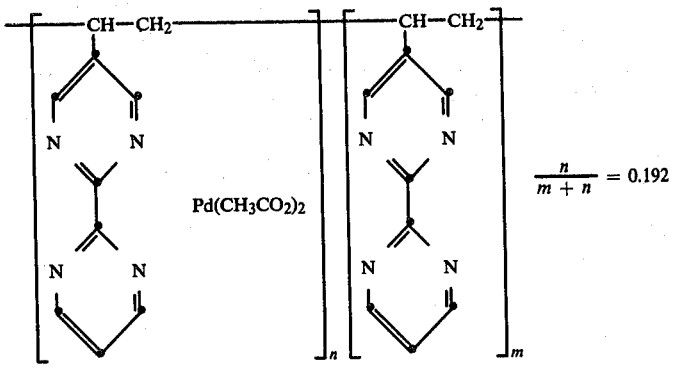

7 ml of tetrahydrofuran are added to a solution of 0.4 g ($2.17 \times 10^{-3}$ moles) of the polymer obtained in Example 17 in water. A solution of 97.4 mg ($4.34 \times 10^{-4}$ moles) of palladium(II) acetate in 10 ml of tetrahydrofuran is added dropwise at 23° C. under an atmosphere of argon. The reaction mixture is stirred for 18 hours and then concentrated to about one third of its volume, while distilling off the water as an azeotrope with dioxan. The yellowish brown precipitate is filtered with suction and dired at 50° C./0.67 Pa.

Analysis for $(C_{14}H_{14}N_4O_4Pd)_n(C_{10}H_8N_4)_m \cdot 1.8(n+m)H_2O$ with $n/n+m=0.192$: calculated: C 50.31%; H 4.80%; N 21.90%; Pd 8.00%. found: C 50.15%; H 4.28%; N 21.72%; Pd 7.92%.

EXAMPLE 20

In accordance with the procedure described in Example 19, 0.4 g of the polymer obtained in Example 17 is reacted with a solution of 1.07 g ($4.78 \times 10^{-3}$ moles) of palladium(II) acetate in 40 ml of tetrahydrofuran. After completion of the reaction the solution is stirred into 800 ml of tetrahydrofuran. The dark brown precipitate is isolated by filtration and dried.

Yield: 1.16 g. Degree of swelling (in tetrahydrofuran): Q=19. The product contains 38.7% by weight of palladium. Molar ratio of N:Pd=2:1.00.

Example 21

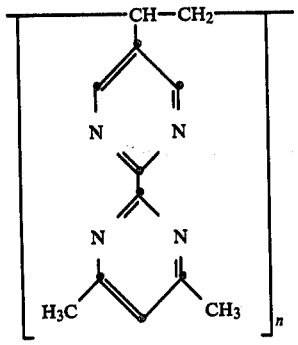

A solution of 2.53 g ($1.19 \times 10^{-2}$ moles) of 4,6-dimethyl-2-pyrimidyl-5-vinylpyrimidine in 70 ml of water is mixed with 9.6 mg (0.3 mole %) of potassium peroxide disulfate and the mixture is polymerised for 24 hours in accordance with Example 16. The resultant suspension is diluted with about 100 ml of water and the precipitate is filtered with suction and washed with water. For purification, the filter residue is dissolved in 150 ml of methanol. The solution is then poured into about 1½ liters of water to give a fine precipitate which is isolated by centrifugation and then lyophilised, affording 1.93 g (76% of theory) of white powder. Intrinsic viscosity (in chloroform): [η]=1.80 dl/g; average molecular weight $\overline{M}_w=860,000$; glass transition temperature Tg=85° C.

Example 22

Copolymer of 2-pyridyl-5-vinylpyrimidine, styrene and divinyl benzene

To 50 ml of a 1% solution of polyvinyl alcohol in water is added a mixture of 3.66 g (0.02 mole) of 2-pyridyl-5-vinyl-pyrimidine, 18.33 g (0.176 mole) of freshly distilled styrene, 0.520 g (0.004 mole) of technical divinyl benzene and 0.099 g (0.6 mmole) of azoisobutyronitrile. The suspension is stirred under nitrogen for 16 hours at 70° C. and for 3 hours at 100° C. (400 rpm). The granular product is filtered with suction, washed with water and allowed to swell for 2 hours in 150 ml of boiling tetrahydrofuran. The mixture is then stirred into 4 liters of water of 75° C. The precipitate is filtered with suction and washed with tetrahydrofuran for 16 hours in a Soxhlet extractor and then dried at 60° C./1.3 Pa. Yield: 15.9 g (70% of theory) of white granular product.

Degree of swelling (in tetrahydrofuran): Q=4.05. Analysis for $(C_{11}H_9N_3)_n(C_8H_8)_m(C_{10}H_{12})_o$ with $n/n+m+o=0.145$ and $o/n+m+o=0.020$: calculated: C 87.63%; H 7.12%; N 5.25%. found: C 87.12%; H 7.16%; N 4.92%.

Example 23

Copolymer of 2-pyrimidyl-5-vinylpyrimidine, styrene and divinyl benzene

A. In accordance with the procedure described in Example 22, 3.68 g (0.02 mole) of 2-pyrimidyl-5-vinylpyrimidine, 18.33 g (0.176 mole) of styrene and 0.520 g (0.004 mole) of technical divinyl benzene are copolymerised. For working up, the reaction mixture is stirred into 2 liters of methanol and the finely particulate product is isolated by centrifugation and allowed to swell in 100 ml of boiling tetrahydrofuran. The resultant gel is then stirred into 4 liters of water of 75° C. and the granular precipitate is washed for 16 hours with tetrahydrofuran in a Soxhlet extractor, the dried at 60° C./1.3 Pa. Yield: 10.2 g (45% of theory) of white product. Degree of swelling (in tetrahydrofuran): Q=3.19.

Analysis for $(C_{10}H_8N_4)_n(C_8H_8)_m(C_{10}H_{10})_o$ with $n/n+m+o=0.02$ and $o/n+m+o=0.02$: calculated: C 91.30%; H 7.64%; N 1.05%. found: C 91.24%; H 7.64%; N 1.04%.

B. To a solution of 1.84 g (0.01 mole) of 2-pyrimidyl-5-vinylpyrimidine, 9.17 g (0.088 mole) of styrene and 0.26 g (0.002 mole) of technical divinyl benzene in 25 ml of N,N-dimethylacetamide are added 25 mg (0.15 mmole) of azoisobutyronitrile and polymerisation is carried out as in Example 16. The resultant oil is purified as described in A. Yield: 9.1 g (81% of theory). Degree of swelling (in tetrahydrofuran): Q=7.85.

Analysis for $(C_{10}H_8N_4)_n(C_8H_8)_m(C_{10}H_{10})_o$ with $n/n+m+o=0.175$ and $o/n+m+o=0.02$: calculated: C 84.90%; H 6.84%; N 8.26%. found: C 84.20%; H 7.29%; N 8.24%.

Example 24

Cobalt(II) complex of poly-{1-[2-(pyrimidin-2-yl)-pyrimidin-5-yl]ethylene}

74 mg ($4 \times 10^{-4}$ moles) of the polymer obtained in Example 17 are dissolved in 13 ml of a mixture of tetrahydrofuran and methanol (3:10). A solution of 117 mg ($4 \times 10^{-4}$ moles) of cobalt(II) nitrate hexahydrate in 3 ml of methanol is then added dropwise at 50° C. A bluish violet precipitate of the polymer cobalt complex is obtained.

Example 25

Cobalt(II) complex of poly-{1-[2-(pyridin-2-yl)-pyrimidin-5-yl]ethylene}

200 mg ($1.09 \times 10^{-3}$ moles) of the polymer obtained in Example 16 are dissolved in 40 ml of a mixture of tetrahydrofuran and ethanol (1:1). A solution of 318 mg ($1.09 \times 10^{-3}$ moles) of cobalt(II) nitrate hexahydrate in 5 ml of ethanol are added dropwise at 60° C. A brownish violet complex of the polymer cobalt complex is obtained.

(B). USE EXAMPLES

Example I

A mixture of 44.4 ml (0.48 mole) of vinyl acetate and 9.77 g (0.08 mole) of benzoic acid is heated to 65° C. Then 163 mg ($3.7 \times 10^{-4}$ equivalents of Pd) of the polymer (catalyst) obtained in Example 18 are added. A sample of the reaction mixture (0.6 ml) is taken after 1, 2, 3, 5, 7, 12, 17, 24 and 30 hours respectively, and the reaction rate is determined by gas chromatography (using 1-chloronaphthalene as internal standard). The time/reaction rate curve shows after 30 hours the maximum yield of vinyl benzoate of 61% (establishment of equilibrium).

The catalyst is isolated by decantation (the supernatant solution contains <5 ppm of palladium), and acetic acid and non-reacted benzoic acid are removed by extraction with aqueous sodium bicarbonate solution. The vinyl benzoate is isolated by fractional distillation. Yield: 7.11 g (60% of theory); b.p. 94° C./1064 Pa.

The catalyst is suspended once more in the mixture of benzoic acid and vinyl acetate and the batch is heated to 65° C., affording again about 7 g of vinyl benzoate after 30 hours.

Example II

The procedure described in Example I is repeated, using as catalyst 460 mg ($3.5 \times 10^{-4}$ equivalents of Pd) of the polymer obtained in Example 19. A 36% yield of vinyl benzoate is obtained after 30 hours.

Example III

The procedure of Example I is repeated, using as catalyst 127 mg ($4.7 \times 10^{-4}$ equivalents of Pd) of the polymer obtained in Example 20. A 37% yield of vinyl benzoate is obtained after 30 hours.

What is claimed is:

1. A compound of the formula I

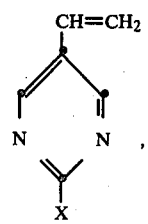

(I)

wherein X is

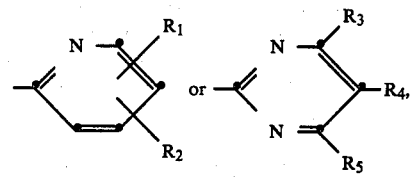

and each of $R_1$ to $R_5$ independently of the other is hydrogen, methyl or ethyl.

2. A compound of the formula I according to claim 1, wherein X has the given meaning, $R_1$, $R_2$ and $R_4$ are hydrogen and $R_3$ and $R_5$ are methyl, or each of $R_1$ to $R_5$ is hydrogen.

3. A compound according to claim 1 of the formula

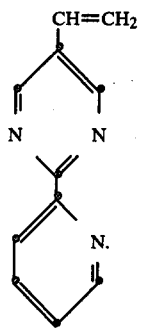

4. A compound according to claim 1 of the formula

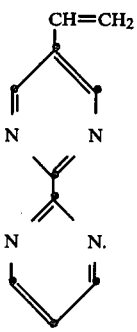

5. A compound according to claim 1 of the formula

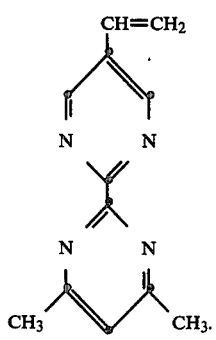 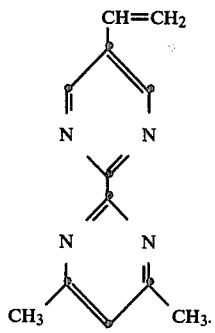
* * * * *